United States Patent
Kassner et al.

(10) Patent No.: US 8,784,875 B2
(45) Date of Patent: Jul. 22, 2014

(54) COLLAGEN FOR USE IN THE TREATMENT OF SKIN DISEASES

(75) Inventors: Anja Kassner, Münster (DE); Martin Trautmann, Dülmen (DE); Sabine Gütt, Hamburg (DE)

(73) Assignee: MedSkin Solutions Dr. Suwelack AG, Billerbeck (DE)

( * ) Notice: Subject to any disclaimer, the term of this patent is extended or adjusted under 35 U.S.C. 154(b) by 10 days.

(21) Appl. No.: 13/305,873

(22) Filed: Nov. 29, 2011

(65) Prior Publication Data

US 2012/0141575 A1   Jun. 7, 2012

(30) Foreign Application Priority Data

Dec. 2, 2010   (EP) ..................................... 10193408

(51) Int. Cl.
*A61F 13/00* (2006.01)
*A61K 38/17* (2006.01)

(52) U.S. Cl.
USPC .......................................... 424/443; 530/356

(58) Field of Classification Search
None
See application file for complete search history.

(56) References Cited

U.S. PATENT DOCUMENTS

| | | | | |
|---|---|---|---|---|
| 4,759,354 A | * | 7/1988 | Quarfoot | ......................... 602/50 |
| 6,830,758 B2 | | 12/2004 | Nichols et al. | |
| 2003/0032601 A1 | | 2/2003 | Kreuter et al. | |
| 2003/0203008 A1 | | 10/2003 | Gunasekaran | |
| 2005/0244482 A1 | * | 11/2005 | Yen et al. | ..................... 424/443 |

FOREIGN PATENT DOCUMENTS

| | | | |
|---|---|---|---|
| DE | 4028622 | | 3/1992 |
| KR | 2009102033 | * | 9/2009 |
| WO | 01/64046 A2 | | 9/2001 |
| WO | 2007/076852 A1 | | 7/2007 |
| WO | 2009/115216 A1 | | 9/2009 |

OTHER PUBLICATIONS

Hart et al., "The role of oxidised regenerated cellulose/collagen in wound repair: effects in vitro on fibroblast biology and in vivo in a model of compromised healing", The International Journal of Biochemistry & Cell Biology 34 (2002) 1557-1570.*
Google Translate—English Machine Translation of DE 4028622; Aug. 30, 2013.*
Espacenet Bibliographic data for DE102004002990 published Aug. 18, 2005, one page.
Espacenet Bibliographic data for DE10350654 published Jun. 2, 2005, one page.

* cited by examiner

*Primary Examiner* — Suzanne M Noakes
(74) *Attorney, Agent, or Firm* — Rankin, Hill & Clark LLP

(57) ABSTRACT

The invention relates to collagen for use in the treatment of inflammatory and degenerative skin diseases and damage to the skin connected therewith, such as in particular in the treatment of psoriasis, dermatitis, neurodermitis, rosacea, urticaria (hives), pruritus (itching), skin eczema and actinic keratosis. In particular, the invention relates to freeze-dried collagen in the form of layered dressings, sheets, pads or masks for the aforementioned use.

9 Claims, No Drawings

COLLAGEN FOR USE IN THE TREATMENT OF SKIN DISEASES

INTRODUCTION

The present invention relates to collagen for use in the treatment of inflammatory and degenerative skin diseases and damage to the skin connected therewith, such as in particular in the treatment of psoriasis, dermatitis, neurodermitis, rosacea, urticaria (hives), pruritus (itching), skin eczema and actinic keratosis. In particular, the invention relates to freeze-dried collagen in the form of layered dressings, sheets, pads or masks for the aforementioned use.

BACKGROUND

Collagen is a biodegradable, biocompatible protein which is widely used in medical applications, for example as a wound healing agent, as carrier material in wound dressings or as a hemostatic.

The use of collagen is also widespread in cosmetics, for example as a moisture-regulating active or auxiliary agent, or as a carrier material for cosmetic dressings.

In particular when collagen is used cosmetically or therapeutically as a carrier material in topical or dermal application, cosmetic or pharmaceutical active, nutrient and/or caring substances for application to or introduction into the skin areas to be treated are generally incorporated into such carrier materials. Such carrier materials doped with active substances are usually referred to as drug delivery formulations, from which the incorporated active agents or substances are released on the treated skin region, thus effecting a caring or healing action in the sense of a cosmetic care treatment or of a therapeutic treatment.

Surprisingly, it was found that collagen itself moreover has an advantageous effect in medical skin treatment, especially in the treatment of inflammatory skin diseases, degenerative skin diseases, as well as damage to the skin connected therewith. In particular, the advantageous effect became evident in the treatment of skin diseases from the group comprising psoriasis, dermatitis, neurodermitis, rosacea, urticaria (hives), pruritus (itching), skin eczema and actinic keratosis. Furthermore, it was found that, in particular, the use of collagen in the form of freeze-dried dressings, sheets or masks, which are re-hydrated or moistened with a suitable activator solution for application, is suitable for treatments given the above-mentioned medical indications.

STATE OF THE ART

Usually, the above-mentioned skin diseases are treated by application of pharmaceutical active substances, such as, in particular, cortisone, analgesics, antihistamines, neuroleptics, in the form of ointments, creams, gels, lotions or shaking tinctures. Treatment by means of baths, fatty/moist wraps or wraps that are soaked in black tea, or by so-called PUVA application (psoralene plus UVA), a combined therapy of psoralene extract and ultraviolet light, is also widespread. Moreover, the treatment of skin diseases such as psoriasis, dermatitis or eczema by means of adhesive occlsive or semi-occlusive bandages or plaster coverings is known, for example from WO 2007/076852 A1 or U.S. Pat. No. 6,830,758 B2.

The disadvantage of such conventional methods of treatment by means of pharmaceutical active substances particularly lies in the side effects, which most frequently are not inconsiderable and often entail persistent long-term damage. The known bath, wrap or PUVA applications are to be considered disadvantageous as they most frequently exhibit very little therapeutic success and may require much effort in application (baths, PUVA). The adhesive occlusive or semi-occlusive bandages or plaster coverings, for example according to WO 2007/076852 A1 or U.S. Pat. No. 6,830,758 B2, have to be considered disadvantageous in particular because they are generally produced from synthetic matrix materials or contain synthetic adhesives, which are based, for example, on polyacrylates. Such synthetic polymatrices and synthetic adhesive materials are often critical with regard to biological compatibility. Moreover, such coverings generally have to be applied over a period of several hours, at least one hour, and most frequently show effects only after several days of regular application. Furthermore, such coverings are most frequently doped with active substances and thus used primarily as a carrier material for applying the active substances to the affected skin areas.

In particular with respect to such adhesive occlusive or semi-occlusive coverings, the freeze-dried collagen preparations according to the invention in the form of layered pads, dressings or masks are advantageous in the treatment of skin diseases such as psoriasis, dermatitis, neurodermitis, rosacea, urticaria (hives), pruritus (itching), skin eczema and actinic keratosis because, on the one hand, they consist of a highly compatible biological material and moreover exhibit an effect already after a significantly shorter covering period and, as a rule, already right after the first treatment, by significantly alleviating the corresponding symptoms of the skin disease.

A method for isolating collagen from marine sponges for producing nano and micro particles from sponge collagen and their use in common semi-solid or liquid pharmaceutical formulations, such as creams or gels, for the treatment of cyclooxygenase-dependent diseases, degenerative skin diseases or damage to the skin, e.g. erythema after UV irradiation and injuries as well as psoriasis or dermatitis, is known from US 2003/032601. Moreover, it is disclosed therein the nano-particular sponge collagen particles, which may also be provided in the freeze-dried form, act as cyclooxygenase inhibitors are have an anti-inflammatory effect, in particular in the case of cyclooxygenase-dependent diseases, as well as an anti-oxidative effect. A corresponding effect for collagen in general, and thus for animal collagen in particular, is not described herein; rather, animal collagen is explicitly referred to as being disadvantageous. Nor are any forms of application of the marine sponge collagen in the form of dressings, pads or similar layered solid forms of application described. Such layered solid forms of administration of collagen distinguish themselves over semi-solid, liquid or cream, gel or lotion-like formulations which contain sponge collagen nano particles more or less as an active constituent by the fact that the collagen can be applied as an active substance in a highly concentrated, more or less highly pure, form.

Besides, there is a comprehensive prior art relating to cosmetic or pharmaceutical skin-treating agents in which collagen is used either as a possible carrier material without any specific action with regard to the indications according to the invention being described therefor, or collagen is mentioned as one of numerous possible active or auxiliary substances in cosmetic or pharmaceutical skin-treating formulations, again without disclosing any advantageous action therefor with regard to any of the indications according to the invention. For example, the semi-occlusive plaster compositions described in the above-mentioned WO 2007/076852 may also contain auxiliary substances for fat replenishment and care which, among others, contain plant and animal extracts and oils, such as collagen, for example. A special action of the collagen itself, in particular in the form of freeze-dried dressings, especially in the treatment of irritated skin and skin diseases in accordance with the present invention is not evident therefrom, either.

From the area of the layered collagen matrices for use in treating skin, cosmetic collagen sponges, e.g. in the form of facial masks, which can be used as drug delivery systems by being doped with suitable active substances, are known from DE 4028622 A1. Thus, collagen is merely disclosed also in this case as a carrier material without any specific action in any one of the indications according to the invention. The collagen materials described therein are also sold for use in cosmetic treatments under the name Matricol® (MATRICOL®). The advantageous effect of MATRICOL® in this case is based on the relaxation of irritated skin, on calming the skin, on a quick easing of erythema as well as on enhancing the regenerative capacity of the skin. Such Matricol® matrices are usually characterized by a collagen content of >90% by wt.

WO 09/115216 A1 describes the use of baobab extracts in treating inflammatory or allergic skin diseases as well as of dry and damaged skin, e.g. due to neurodermitis, pruritus, psoriasis or similar complaints, wherein the active-agent extracts according to the invention can be applied in one embodiment by means of layered, freeze-dried collagen matrices. However, the collagen matrices are disclosed also in this case only as carrier materials without any specific suggestion of any inherent positive effect in the treatment of the claimed indications.

Drug delivery pads of nano-structured fiber networks, in particular of bacterially synthesized cellulose that cause a strong cooling effect and which are moreover suitable for the application of active substances, with collagen being cited, among others, in the group of possible active substances, are the subject matter of DE 102004002990 A1. Moreover, the use of the pads according to the invention for the topical treatment of injuries, painful tissue damage and neurodermitis or eczema is described, with the positive effects with regard to these indications being ascribed, however, to the special cooling effect of the matrices according to the invention. A specific suggestion as to the additional active substance "soluble collagen", which is cited by way of example, also exerting a positive effect with regard to corresponding indication, is also not apparent from this.

OBJECT

The object of the present invention lay in providing improved treatment means for the treatment of inflammatory and degenerative skin diseases as well as of damage to the skin connected therewith, such as, in particular, psoriasis, dermatitis, neurodermitis, rosacea, urticaria (hives), pruritus (itching), skin eczema and actinic keratosis, including the symptoms respectively associated therewith. The advantageous action of the collagen, in particular in the form of freeze-dried dressings, masks or pads, which was surprisingly found within the context of the present invention with regard to the above-mentioned medical indications was in this case neither known in nor obvious from the prior art.

DESCRIPTION OF THE INVENTION

Inflammatory skin disease in the sense of the invention include, for example, systemic inflammatory skin diseases, cyclooxygenase-dependent inflammatory skin diseases and locally induced inflammatory skin diseases such as those, for example, that occur as a consequence of a local treatment of actinic keratoses with immunostimulants, such as, for example, imiquimod, or inflammatory and allergic skin diseases, e.g. allergic skin reactions, as a consequence of intolerance reactions or side effects due to medical treatments, including the symptoms and epiphenomena respectively associated therewith. In this case, inflammatory skin diseases are substantially characterized by the following direct signs of inflammation or symptoms at the site of inflammation: erythema, overheating, swelling, pain and limited function, with these signs of inflammation not always being directly recognizable or even only partially detectable. Frequent epiphenomena of inflammatory skin diseases include the formation of edema, formation of blisters, pustules or wheals, formation of eczema as well as pruritus (itching), which do not occur inevitably. It is also possible that only one or more of these epiphenomena occur. In addition, further unspecific signs of inflammation in the form of general reactions of the entire organism can occur, depending on severity, such as fever, a general feeling of being unwell, leukocyte level increase or drop, CRP-level increase, accelerated erythrocyte sedimentation or procalcitonin-level increase. In this case, the collagen used according to the invention preferably has a positive, in the sense of healing or alleviating, action on the direct inflammatory signs such as erythema, overheating (heat or burning), swelling, feeling of tightness, pain and limited function, as well as in particular on the possible epiphenomena formation of edema, formation of blisters, pustules or wheals, formation of eczema as well as, in particular, on pruritus (itching). Inflammatory skin diseases also include, for example, acne.

Degenerative skin diseases include, for example psoriasis, dermatitis (in particular also atopical dermatitis/neurodermitis), rosacea, urticaria (hives), actinic keratosis and eczema of the hands, including the respectively associated symptoms.

Damage to the skin within the sense of the present invention in principle relate to dysfunctions or impairments of the natural physical and mechanical protective and/or barrier properties of the skin and generally include damage to the skin caused by physical (mechanical or thermal stimuli or radiation), chemical (acids, lyes, toxins allergens) or biological stimuli, in particular also dry, chapped, scaly or scabby skin changes, as well as skin changes characterized by the formation of papules, nodes, vesicles, blisters, pustules, wheals (urtica), scales (squama), crusts (crusta), fissures (rhagade), formation of erythema, e.g. also in conjunction with teleangiectases (visibly expanded capillaries of the skin or also of the upper dermis), which occurs especially in the case of rosacea, or erythema after cold stimulation such as by cryotherapy, for example by means of liquid nitrogen, e.g. in the treatment of actinic keratosis, as well as eczematous changes of the skin, also in the form of the formation of blisters, wheals or pustules, allergic skin changes as well as dermatoses in general. Furthermore, such damage to the skin can also be caused by cosmetic or medical treatment with mechanical, chemical, physical or thermal stress, as mentioned above by way of example.

By way of clarification, it should be noted that the assignment of the described disorders, symptoms or epiphenomena to individual ones of the described skin diseases included according to the invention is not an exclusive assignment. Rather, many of the aforementioned symptoms or disorders can occur in connection with almost all of the aforementioned clinical pictures. For example, erythema (reddening), overheating, pruritus (itching), eczematous changes or scaling, which can occur in various degrees of intensity, are direct symptoms or epiphenomena of, for example rosacea, psoriasis, dermatitis, neurodermitis, dermatoses, eczema, etc.

In this case, in particular the following positive effects were observed during the application according to the invention in the case of the above-described indications or the described symptoms:

Accelerated easing of symptoms and accompanying pain-relieving action
Effect of relieving pruritus to the extent of making it disappear (calming the skin)
Persistent pruritus-relief
Long-term cooling action/reduction of heat or burning
Anti-swelling action
Reduction of feeling of tightness
Easing of erythema
Improved skin moisturization
Reduction of scaling and cracked skin due to dryness
Increased elasticity of the skin (skin surface becomes more elastic and less tight)
Improved functional performance of the affected body parts (e.g. improvement of the mobility of affected joint regions, such as fingers, elbows, knees etc.)
Skin has a pleasant feel during and after application
Skin has an improved feel after application
High tolerance/Biocompatibility In particular during the acute treatment of pruritus (itching), most frequently as a symptom or epiphenomenon of one of the aforementioned diseases or disorders, by means of the use according to the invention preferably of layered collagen materials, the following positive effects and advantages become evident as compared with conventional treatment methods, which usually take place in the form of creaming treatments:

Primary Effects:
Immediate alleviation of itching to the extent of making it disappear
Calming of the skin
Relief of the acute complaints
Reduction of the erythema which most frequently accompanies the pruritus
Skin care (optionally also by means of further skin care substances contained in the collagen material)
Secondary Effects:
The impulse to scratch is inhibited by the physical barrier by applying a protective layer on the affected regions of the skin in the form of a layered dressing; acute irritation of the skin is thus reduced, and additional mechanical damage to the skin (due to scratching) is prevented. In contrast, creams as a rule amplify the impulse to scratch oneself, because of the manual application
The covered skin is given time to "relax"
Tertiary Effects:
Itching can be considered an "invisible" symptom of a disease; by applying a clearly visible product, the disease of the patient is recognized (psychological effect)

According to the invention, the use of collagen is preferred in the treatment of psoriasis, dermatitis, neurodermitis, atopical dermatitis, rosacea, urticaria (hives), pruritus (itching), skin eczema or eczematous changes, erythema and actinic keratosis as well as of persistent inflammatory lesions after the completion of a local treatment of actinic keratosis with immunostimulants, as well as, respectively, the symptoms associated therewith.

The use of collagen is particularly preferred in the treatment of psoriasis, dermatitis, neurodermitis, atopical dermatitis, rosacea, urticaria (hives), pruritus (itching) as well as of persistent inflammatory lesions after the completion of a local treatment of actinic keratosis with immunostimulants, as well as, respectively, the symptoms associated therewith.

In this case, the use of collagen is very much preferred in the treatment of neurodermitis, atopical dermatitis, rosacea, urticaria (hives), pruritus (itching) as well as of persistent inflammatory lesions after the completion of a local treatment of actinic keratosis with immunostimulants, as well as, respectively, the symptoms associated therewith.

The use according to the invention in the treatment of pruritus (itching) is most preferred.

The surprising advantageous effect in the treatment of the above-mentioned medical indications or symptoms was observed in particular for collagen selected from the group of animal collagen. This is preferably obtained from collagen sources of bovine, equine and porcine origin, with bovine collagen being very much preferred. The collagen can be obtained with the usual methods from the usual sources such as skins or tendons, and can preferably be processed and produced in accordance with the methods known from the prior art and, for example, from DE 4028622 A1 or DE 10350654 A1.

The collagens and collagen materials preferred according to the invention are characterized, in particular, by excellent hydrating properties and a good moisture absorbing capacity or absorbency. Due to the structural similarity to human skin and human tissue, collagen types occurring in skin and tissue are preferably selected, in particular collagen of the types I, III and V. This is the reason for the particularly good tolerance and biocompatibility of such collagens according to the invention.

Another embodiment relates to such collagens that comprise the following fractions:
a) fibrous insoluble collagen
b) natively soluble (acid-soluble) collagen and
c) collagen peptides.

Fibrous insoluble collagen according to fraction a) is considered to be the fraction of a collagen suspension which is insoluble in an acid solution of pH<4, which can be precipitated by centrifuging at 16,000 g, and which contains fibers that are visible in a light microscope (fiber thickness from 0.2 µm).

Natively soluble or acid-soluble collagen refers to the content of collagen which forms a clear solution in an acid solution at pH<4 and which contains no fiber structures that are discernible under a light microscope. The natively soluble or acid-soluble collagen can be separated into higher-molecular, complete collagen molecules with a molecular weight>250 kDa, corresponding to fraction b), and low-molecular collagen peptides with a molecular weight>250 kDa, by fractionation, for example by means of SEC (size-exclusion chromatography).

Thus, the aforementioned fraction b) denotes natively-acid-soluble, higher-molecular, complete collage molecules with a molecular weight>250 kDa.

Collagen peptides according to fraction c) accordingly comprise the low-molecular part of the acid-soluble fraction, which, having a molecular weight of <250 kDa cannot be associated with any complete collagen molecule.

The presence of soluble complete collagen molecules as well as of the low-molecular peptide constituents can be proved qualitatively by analysis of the soluble constituents by means of the known protein-chemical methods, for example by SDS-PAGE.

When using the collagens according to the invention, in particular if they are provided in the form of rehydratable freeze-dried layered collagen matrices, soluble components are released from the fractions b) and c) during application, and they can act directly on the site of application. This is advantageous in that such soluble collagen fractions and low-molecular peptide constituents have a film-forming effect and thus improve the water-retention capacity of the skin and accordingly reduce transepidermal water loss.

Moreover, it is also possible to use collagen which was subjected to a cross-linking reaction. In this case, a thermal cross-linking, so-called dehydro-thermal cross-linking, is preferred. Moreover, cross-linking with chemical cross-linking agents is possible. This includes, in particular, aldehydes, such as glutaraldehyde; carbodiimides, such as EDC; isocyanates; epoxides or imidazoles, with di- and polyfunctional epoxides from the group of the chemical cross-linking agents being particularly preferred.

For the use according to the invention, which generally takes place topically or externally, the use of collagen in the form of solid, dry or pre-moistened, absorbing or hydratable preparations, in particular in the form of layered, flat dressings, is particularly suitable. Thus, it is preferred according to the invention to use the collagen in the form of masks, sheets, matrices, dressings, pads, layers or other flat forms for the indication according to the invention, because such embodiments are particularly suitable for the external and extensive treatment also of larger affected regions of the skin. Moreover, collagen in the form of porous, sponge-like, rehydratable, hydrophilic embodiments is preferably used in this case.

Freeze-dried collagen is used particularly preferably, freeze-dried layered collagen matrices or dressings are very much preferred. The use of freeze-dried collagen matrices is preferred it is possible with them to make collagen preparations available that are substantially free of preservatives and/or perfume substances. Preservatives and perfume substances are known for their skin-irritating and irritating potential and can have a negative influence on the success of the treatment, due to the skin disease and disorders according to the invention, in particular if the skin is already damaged. Accordingly, such embodiments are particularly preferred according to the invention which are substantially free of preservatives and/or perfume substances.

The collagen materials or preparations used according to the invention consist of at least 50% by wt. collagen, preferably of at least 75% by wt. collagen, more preferably of at least 85% by wt. collagen, particularly preferably of >90% by wt. collagen.

Such solid, layered, rehydratable collagen matrices, preferably in the form of freeze-dried porous, sponge-like collagen matrices, are characterized by a high capacity for absorbing and retaining liquid. This can be ascribed, on the one hand, to the high liquid deposition capacity in the porous sponge structure of such matrices, and on the other hand to the capacity of the collagen to bind large amounts of water in the form of hydration sheaths to the collagen fibers and fibrillas. A long-term skin moisturization and a high moisture deposition into the treated skin tissue is thus supported, which has an advantageous effect on the elasticity, skin moisturization and smoothing of the skin. In addition, a long-term uniform evaporation action on the application site and thus a permanent, uniform and persistent cooling can be brought about by this effect of such porous, sponge-like layered collagen matrices, which is advantageous in particular in the case of skin areas that are overheated and have a high blood supply due to inflammatory reactions, the sensations of heat and tightness as well as in the case of pruritus (itching) and skin diseases accompanied by itching.

Basically, layered collagen materials can be provided in any desired geometrical shape and size, or be individually cut into the shape of the skin area to be treated. For optimum applicability, layered collagen materials are particularly suitable which have a layer thickness (shortest side length) of a maximum of 8 mm, preferably up to 5 mm, more preferably of up to 3 mm.

The collagens, collagen matrices and collagen preparations used according to the invention, in particular those in the form of freeze-dried layered matrices, have a pH value of <7. Preferably, the pH value is <6, particularly preferably <5. Such an acid pH value is due, on the one hand, to the above-mentioned production methods, and is also desired because such pH values match or come close to the natural pH value of the skin. The low pH values preferred according to the invention in particular have a beneficial effect upon the improvement and regeneration of the natural acid protection layer of the skin. It is known that the pH value of the skin is greatly increased and can generally rise to pH 8 in the case of skin diseases such as, for example, neurodermitis, which indicates damage to the acid protection layer. Thus, the collagens, collagen matrices and collagen preparations with the preferred acid pH values according to the invention are in particular suitable for the treatment of skin diseases that are accompanied by an increased pH value or damage to the acid protection layer, such as, for example, neurodermitis.

Moreover, the use of the layered collagen matrices according to the invention is particularly preferred because the collagen is thus more or less applied in a highly concentrated manner and the combination of its advantageous properties can cooperate optimally in the use according to the invention, which is what makes the surprising effects possible in the first place. Such layered collagen matrices in particular have a synergetic effect because of the special hydration properties for the improvement of skin moisturization by means of a high moisture deposition in the skin and the improvement of the elasticity as well as the intensive cooling, the preferred low pH value for the regeneration of the natural acid protection layer of the skin and the release of soluble collagen and peptide constituents for increasing the water retention capacity and thus the reduction of transepidermal water loss, as well as the infiltration of skin-like collagen and peptide constituents for improving elasticity and regeneration of the affected skin. A combination of these advantageous properties cannot be obtained with the materials and preparations known from the prior art for the treatment of the skin diseases according to the invention, and the significant improvements with regard to the action that could be obtained therewith were not foreseeable to this extent, and were therefore surprising.

The collagens used according to the invention can be provided, according to the invention, in the form of collagen preparations, preferably in the form of solid, dry collagen preparations which moreover contain at least one active and/or auxiliary substance. Such collagen preparations are available on the market as cosmetic treatment agents, for example under the name Matricol®, as was mentioned above.

Active substances in particular include cosmetic or therapeutic or pharmaceutical active substances suitable for external use. Cosmetic active substances within the sense of the invention are substantially agents within the sense of the German Food and Feed Code (LFGB), i.e. substances or preparations from substances that are intended for external application on humans for cleaning, care or influencing appearance or body odor, or for conveying olfactory impressions, unless they are primarily intended for alleviating or eliminating disease, disorders, bodily defects or pathological complaints.

Examples of cosmetically, or optionally, for example, dermatologically therapeutically effective compounds include: anti-acne agents, antimicrobial agents, antitranspiration agents, astringent agents, deodorizing agents, depilatory agents, conditioning agents for the skin, skin-smoothing agents, agents for increasing skin hydration, such as dexpanthenol (panthenol, pantothenol), glycerin or urea, sun blockers, keratolytic agents, free-radical scavengers for free radicals, antiseborrhoeic agents, anti-dandruff agents, antiseptic active substances, active substances for treating signs of the aging of the skin and/or agents modulating the differentiation and/or proliferation and/or pigmentation of the skin, vitamins such as vitamin C (ascorbic acid) and its derivatives, e.g. glycosides such as ascorbyl glucoside or esters of ascorbic acid, such as sodium or magnesium ascorbyl phosphate or ascorbyl palmitate and stearate, L-ascorbic acid phosphate esters, alkaline metal salts, such as sodium and potassium salts of L-ascorbic acid phosphate esters; earth-alkaline metal salts such as magnesium and calcium salts of L-ascorbic acid phosphate esters; trivalent metal salts such as aluminum salts of L-ascorbic acid phosphate esters; alkaline metal salts of L-ascorbic acid sulfate esters, such as sodium and potassium salts of L-ascorbic acid sulfate esters; earth-alkaline metal salts such as magnesium and calcium salts of L-ascorbic acid sulfate esters; trivalent metal salts such as aluminum salts of L-ascorbic acid sulfate esters; alkaline metal salts, such as sodium and potassium salts of L-ascorbic acid esters; earth-alkaline metal salts such as magnesium and calcium salts of L-ascorbic acid esters; and trivalent metal salts such as aluminum salts of L-ascorbic acid esters. Alpha-hydroxy acids, β-hydroxy acids, alpha-keto acids, β-keto acids, retinoids (retinol, retinal, retinic acids), anthralins (dioxanthranol), anthranoids, peroxides (in particular benzoyl peroxide), minoxidil, lithium salts, antimetabolites, vitamin D and its derivatives; catechins, falvonoids, ceramides, polyunsaturated fatty acids, essential fatty acids (e.g. gamma-linolenic acid), enzymes, coenzymes, enzyme inhibitors, hydrating agents, skin-soothing agents, detergents or foam-forming agents, and inorganic or synthetic matting fillers, or decorative substances such as pigments or colorants and particles for foundations, make-up formulations, and other agents for cosmetic beautification and coloring of the eyes, lips and face, as well as abrasive agents.

Moreover, plant substance extracts or extracts obtained therefrom or individual substances can be mentioned. Generally, the plant active substance extract is regularly selected from the group consisting of solid plant extracts, liquid plant extracts, hydrophilic plant extracts, lipophilic plant extracts, individual plant ingredients; and their mixtures, such as flavonoids and its aglycones: rutin, quercitin, diosmin, hyperoside, (neo)hesperidine, hesperitine, ginkgo biloba (e.g. ginkgo flavone glycosides), crataegus extract (e.g. oligomer procyanidines), buckwheat (e.g. rutin), sophora japonica (e.g. rutin), birch leaves (e.g. quercitin glycosides, hyperoside and rutin), elderberry blossoms (e.g. rutin), lime blossom (e.g. essential oil with quercitin and farnesol), oil of St. John's wort or extract of St. John's wort, evening-primrose oil, (e.g. olive oil extract), calendula, arnica, (e.g. oily extracts of the blossoms with essential oil, polar extracts with flavonoids), melissa (e.g. flavones, essential oils), immunostimulants: echinacea purpurea (e.g. alcoholic extracts, fresh plant juice, press-juice), eleutherococcus senticosus; alkaloids: caffeine, theine, black tea or black tea extract, theobromine, capsacine, rauwolfia (e.g. prajmaline), vinca (e.g. vincamin); other phytopharmacons: aloe, horse chestnut (e.g. aescine), garlic (e.g. garlic oil), pineapple (e.g. bromelaines) ginseng (e.g. ginsenosides), silybum marianum fruits (e.g. extract standardized to silymarin), Butcher's broom wort (e.g. ruscogenin), valerian (e.g. valepotriates, Tct. valerianae), kava-kava (e.g. kava-lactone), hop (e.g. hop bitter substances), extr. passiflorae, gentian (e.g. ethanolic extract), anthraquinone-containing drug extracts, e.g. aloin-containing aloe vera juice, pollen extract, algae extract, liquorice extracts, palm extracts, galphimia (e.g. mother tincture), mistletoe (e.g. aqueous-ethanolic extract), phytosterols (e.g. beta-sitosterin), common mulleins (e.g. aqueous-alcoholic extract), drosera (e.g. liqueur-wine extract), sea-buckthorn fruits (e.g. juice obtained therefrom or sea-buckthorn oil), marshmallow root, primrose-root extract, fresh plant extracts from mallow, comfrey, ivy, horsetail, yarrow, ribwort (e.g. pressed juice), stinging nettle, celandine, parsley; plant extracts from norolaena lobata, tagetes lucida, teeoma siems, momordica charantia and aloe-vera extracts, cardiospermum mother tincture, dulcamara extract, as well as tanning agents such as tannin.

In contrast to the above described active substances, which are substantially used in cosmetics, the therapeutically active substances (medicaments) are such active substances which, within the meaning of the "Arzneimittelgesetz" (German Medical Preparations Act), are intended among other things to cure, to ease or to prevent diseases, illnesses, bodily damage or pathological complaints. According to the invention, in particular such agents or active substances are suitable which are intended for external dermal or transdermal application, in particular in the area of skin treatment and healing.

Active substances for dermal or transdermal application use are in particular skin-active, but also transdermal active substances. They include, for example: agents for the treatment of burns, agents for the treatment of skin diseases, externally applicable analgesics, e.g. dextropropoxyphene, pentazocine, pethidine, buprenorphine; antirheumatics/antiphlogistics (anti-inflammatory agents) (NSAR), e.g. frankincense or frankincense extract, indomethacin, diclofenac, naproxen, ketoprofen, ibuprofen, flurbiprofen, salicylic acid and salicylic-acid derivatives such as acetylsalicylic acid, oxicams; steroid hormones, e.g. corticoids and glucocorticoids, such as hydrocortisone, cortisol, cortisone acetate, cloprednol, prednisone, prednisolone, deflazacort, fluocorolone, triamcinolone, betamethasone, betamethasone velerate, mometasone furoate, dexamethasone, methylprednisolone, ethynyl estradiol, medroergotamine, dihydroergotoxine; gout remedies, e.g. benzbromarone, allopurinol; external dermatological agents, antihistamines such as bromopheniramine, bamipine; antibiotics such as erythromycine, clindamycine, tetracycline, including antibacterial agents, such as e.g. colloidal silver and silver salts, such as silver chloride, silver nitrate, silver iodide or other silver-containing wound-treating agents known from the prior art; antimycotics; peptide medicaments; antiviral active substances; anti-inflammatory active substances, antipruritic active substances, such as e.g. anaesthetizing active substances, antihistamines, benzocaine, polidocanol or corticoids and glucocorticoids; anti-acne agents, antiparasitic active substances; externally applicable hormones; venous therapeutic agents; immunosuppressives such as calcineurin inhibitors such as tacrolimus and pimecrolimus, mineral substances and trace elements, such as e.g. inorganic or organic selenium compounds, zinc and zinc salts, etc., all for dermal or transdermal application.

By way of clarification, it should be noted that the classification of the active substances into the group of the cosmetically or therapeutically active substances within the context of the present invention is not an exclusive assignment. In particular, the classification made herein does not rule out the possibility that the corresponding active substances are used both as cosmetic as well as therapeutic active substances.

Preferred active substances for dermal and transdermal application are selected from the group including: agents for the treatment of skin diseases such as neurodermitis, atopical dermatitis, psoriasis, rosacea etc., inflammation-inhibiting active substances, antipruritic active substances, tanning agents, topical analgesics, anesthetic agents and anti-bacterial active substances. Particularly preferred active substances are selected from amongst silver-containing active substances, such as, in particular, silver nitrate, silver chloride, micro-silver particles, tacrolimus, pimecrolimus, antihistamines, polidocanol, frankincense/frankincense extract, capsaicine, tannin, St. John's wort oil/extract, evening-primrose oil, dexpanthenol as well as inorganic or organic selenium compounds, zinc and zinc salts.

Very particularly preferably, at least one active substance is selected from the group of the skin-like lipids, comprising, for example, phospholipids, neutral lipids and sphingolipids as well as components of the natural moisture-retaining factor of the skin, the so-called natural moisturizing factor (NMF), comprising for example urea, amino acids and carboxylic acids, pyrrolidone carboxylic acid, sodium, potassium, calcium, magnesium, lactate (lactic acid), citrate, chloride, phosphate etc., urea and other organic acids.

The collagens used according to the invention, in particular those in the form of collagen preparations, can moreover contain at least one auxiliary substance.

Auxiliary substances include: pH-adjusting agents, such as buffering substances, inorganic and organic acids or bases; fatty substances, such as mineral oils, such as paraffin oils or Vaseline oils, silicone oils, vegetable oils such as coconut oil, almond and sweet almond oil, apricot oil, corn oil, jojoba oil, olive oil, avocado oil, sesame oil, palm oil, eucalyptus oil, rosemary oil, lavender oil, pine oil, thyme oil, mint oil, cardamom oil, orange-blossom oil, soybean oil, bran oil, rice oil, rapeseed oil and castor oil, wheat-germ oil and vitamin E isolated therefrom, evening-primrose oil, vegetable lecithins (e.g. soybean lecithin), sphingolipids/ceramides isolated from plants, animal oils or fats, such as tallow, lanolin, butyric oil, neutral oil, squalane, fatty-acid esters, esters of fatty alcohols such as triglycerides, and waxes with a melting point corresponding to skin temperature (animal waxes such as beeswax, carnauba wax and candelilla wax, mineral waxes, such as microcrystalline waxes, and synthetic waxes, such as polyethylene waxes or silicone waxes), as well as all oils that are suitable for cosmetic purposes (so-called cosmetic oils), such as, for example, those mentioned in the CFTA treatise entitled Cosmetic Ingredient Handbook, 1st edition, 1988, The Cosmetic, Toiletry and Fragrance Association, Inc., Washington, surfactants in addition to the above-mentioned washing tensides, such as dispersants, wetting agents, emulsifiers etc.; fillers; stabilizers; cosolvents; pharmaceutically and cosmetically commonly used or other colorants and pigments, in particular those that are used primarily for the color design of the collagen composition and not for application and color design on the human body, such as those pigments and colorants as those decorative colorants; preserving agents; softening agents; lubricants listed in the group of cosmetic active substances. However, for the above-mentioned reasons, auxiliary agents from the group of preservatives are less preferred.

Auxiliary substances preferred according to the invention are fats and oils. This includes in particular cosmetic oils as cited above, in particular triglycerides, particularly preferably caprylic/capric acid triglycerides, squalane or jojoba oil as well as evening-primrose oil.

From the group of the fats and oils, those skin-like lipids mentioned in the above-defined group of active substances are particularly preferred that can be classified into the subgroups polar lipids, neutral lipids and sphingolipids. In the group of polar lipids, particular mention is to be made of phospholipids and cholesteryl sulfate; the preferred neutral lipids include squalane, squalene, triglycerides, wax esters, sterols (e.g. cholesterol) and both saturated and unsaturated free fatty acids, preferred sphingolipids include in particular the entire group of ceramides.

Generally, the classification of the above-mentioned substances into the category of auxiliary substances within the context of the present invention does not preclude these auxiliary substances from also having certain cosmetic and/or therapeutic effects, which especially applies for the preferably used cosmetic oils mentioned. In particular the preferred skin-like lipids mentioned in the group of the active substances are, in principle, equally included in the groups of fats and oils mentioned among the auxiliary substances.

A particular embodiment relates to the use according to the invention of collagen or a collagen preparation within the sense of the present invention, which is substantially free from auxiliary agents selected from the group of preservatives and perfume substances as well as of polyethers, such as in particular from the group of polyethylene glycols (PEGs), polypropylene glycols (PPGs) and polyglcols (PGs).

Furthermore, the layered collagen matrices and preparations can also be laminated or provided in the form of multilayered interconnected layers ("sandwich-layer"). The laminates used may include the usual materials known from the prior art, such as, for example, fibers, non-wovens, nets, films or foils of suitable materials such as, for example, rayon, cellulose, polyethylene (PE) or polyurethane (PU) or other synthetic or semi-synthetic polymers/copolymers which can be firmly connected to the carrier materials in the sense of the present invention by conventional methods, such as gluing, heat-laminating, cross-linking etc. Such a lamination is particularly suitable to improve mechanical stability of the layered collagen materials according to the invention as well as their handling properties during application, particularly in the moistened state. A preferred lamination includes a lamination with an adhesive layer or a layered plaster material which is preferably attached to the layered collagen materials in such a way that the adhesive laminate layer, at the edges, protrudes completely or partially over the collagen material so that the laminated collagen materials can be fixed to the skin areas to be treated relatively easily by means of the adhesive lamination that protrudes at the edges, similar to a conventional plaster arrangement. In the case of such adhesive laminated collagen materials, such adhesive lamination coatings are particularly preferred which have a particularly good skin compatibility, low tendency to irritate and cause allergies, as well as a capacity to be easily detached, in order not to additionally irritate the already damaged or irritated skin areas when detaching the adhesive layer. Moreover, in particular such adhesive lamination coatings are preferred which are hydrophilic and non-occlusive or at most semi-occlusive in order to enable the moisturization of the laminated collagen materials for application. Occlusive lamination coatings are not preferred because they do not enable any evaporation and are thus disadvantageous with regard to the advantageous effect of evaporation and thus the long-term cooling of the collagen materials according to the invention. Moreover, when selecting such adhesive lamination coatings, attention has to be paid that the adhesive layer is not water-soluble, so that the adhesive cannot be dissolved out from the material when it is moistened and so that the adhesive and fixing effect is not lost.

Thus, the present invention also comprises, in particular, such collagen materials which comprise an additional layer of fibers, non-wovens, nets, films or foils or an adhesive layer, with this additional layer covering the collagen material partially or completely and being applied on the layered collagen material in such a way that it ends flush with the edges thereof or protrudes completely or partially over the collagen material at the edges.

In the use according to the invention of collagen or collagen preparations in the preferred forms of application of layered dry dressings, pads or masks, the treatment substantially comprises the following steps:
a) providing a layered dry form of application consisting of collagen or a collagen preparation
b1) moistening the dry layered collagen material with an aqueous solution, and applying the moistened collagen material to the skin areas to be treated
or
b2) applying the dry layered collagen material to the skin areas to be treated, and moistening the dry layered collagen material on the skin areas to be treated.

In principle, the moistened collagen materials can in this case remain on the skin area to be treated until they are completely dry. However, the moistened layered collagen materials are preferably kept on the skin for no longer than 60 minutes, more preferably for up to 45 minutes. The moistened layered collagen materials are preferably kept on the skin for at least 5 minutes, more preferably for at least 10 minutes, particularly preferably for at least 20 minutes. Then, the collagen materials, which as a rule are still moist, are taken off and then another conventional care treatment of the treated skin areas can be optionally carried out with the usual care products.

During the use according to the invention of such layered moistened collagen materials, moistening or rehydration of the layered—preferably freeze-dried—collagen materials takes place, for example, as described above in step b1) or b2), with an aqueous solution selected from the group comprising water as well as, optionally, demineralized water or so-called thermal water, physiological solutions (e.g. physiological saline solutions) as well as aqueous solutions containing at least one active and/or auxiliary substance. The aqueous solutions used for moistening or rehydration are also referred to as activator solutions.

Such activator solutions can be, for example, solutions of highly volatile active and/or auxiliary substances, which should not or cannot be introduced into a freeze-dried material because of the production process, e.g. freeze drying, such as certain parts of essential oils, perfumes, etc. Moreover, such active and/or auxiliary substances can be contained which have an additional moisturizing effect, and which due to this moisturizing effect or due to hygroscopic tendencies cannot be incorporated, or only in small amounts, into the freeze-dried preparations preferred according to the invention, because either the stability of the freeze-dried collagen materials itself or the stability of possibly contained moisture-labile active substances thus cannot be maintained any longer.

In principle, one or more of the above-mentioned active and/or auxiliary substances can be contained in the activator solutions. In particular, active substance-solutions are particularly suitable which contain one or more of the abovementioned preferred active or auxiliary substances for the therapeutic application in the indications according to the invention.

In a particularly preferred embodiment, an aqueous activator solution is used which is substantially free from emulsifiers, preservatives, perfume substances and/or auxiliary substances from the group of polyethers, polyethylene glycols (PEGs), polypropylene glycols (PPGs) and polypropylene glycols (PGs).

In another preferred embodiment of the invention, the collagen material according to the invention is provided together with the activator solution in a combined spatial arrangement (application package, set, kit-of-parts etc.). Such kit-of-parts combinations preferably comprise at least one of the collagen materials according to the invention, preferably such materials in the form of layered dressings, pads or masks, as well as at least one aqueous solution containing one or more active substances and/or one or more auxiliary substances (activator solution).

The configuration of such kit-of-parts combinations of, on the one hand, collagen material according to the invention and, on the other hand, the activator solution can provide that the two components are removed separately from the kit-of-parts arrangement and are combined and dissolved outside of it for further use. It is also conceivable, however, that a combination of the components is carried out within the kit-of-parts packaging itself, e.g. in compartments provided for this purpose, and that the rehydrated composition is then directly supplied from it to the further external or transdermal use. Preferably, this can be done directly by the end user.

According to the invention, the use of the collagen materials preferably takes place externally or dermally or topically.

By way of clarification, it should be noted that within the context of the present invention, the different embodiments of the collagen are also collectively referred to by the term "collagen material".

The present invention is illustrated in more detail by the following examples. The examples merely constitute exemplifications, and the person skilled in the art is capable of extending the specific examples to other embodiments claimed.

EXAMPLES

Example 1

Use of Freeze-Dried Layered Collagen Matrices in the Treatment of Neurodermitis

The treatment of neurodermitis existent since birth in a male patient (age: 39 years) took place with various embodiments of layered freeze-dried collagen materials according to the present invention.
The following was used:
a) Layered freeze-dried collagen matrices of pure (bovine) collagen (100% by wt. collagen) (without any further active or auxiliary substances) that can be obtained in accordance with the method described as being preferred according to the invention
b) Various commercially available layered freeze-dried collagen preparations of the brand Matricol®, each containing >90% by wt. collagen, as well as various common active and/or auxiliary substances as defined within the context of the present invention, such as dexpanthenol, green tea-extract, caviar extract, squalane, cosmetic fats and oils.

Prior to the application of the collagen material, the skin was in each case severely reddened and tight and itched severely For the treatment, the layered collagen materials were cut to the size of the affected skin areas, laid in a dry state on the skin to be treated, and moistened to saturation by spraying with water (tap water). The rehydrated collagen dressings were kept on the affected skin regions for a period of approx. 30 min.

During this treatment, a clear fading of the reddening was evident, as was a significant alleviation of the itching sensation. The treated skin was relaxed and its functional performance was thus significantly improved. These positive effects of the treatment persisted over at least 6 h; if the treatment was repeated, even over 12 h.

The effects observed were equally evident both in the case of pure collagen materials with 100% by wt. collagen according to a), as well as in various active/auxiliary substance-containing Matricol®-variants with a collagen content of >90% by wt. in accordance with b).

Example 2

Use of Freeze-Dried Layered Collagen Matrices in the Treatment of Rosacea

The treatment took place within the context of a clinical trial (study/observation of application) by means of commercially available layered freeze-dried collagen preparations of the brand Matricol® with a collagen content>90% by wt.

Within the context of the trial, 10, patients aged between 24 and 79 years with slight intensity (rosacea diathesis and rosacea erythematosa-teleangiectatica) or severe intensity (rosacea papulopusfulosa) rosacea each carried out up to 6 individual observations of application. In total 41 individual applications were carried out by the 10 patients, with 4 cases of application in which patients did not document the result after 24 hours.

For this purpose, patients assessed the following parameters about 15 minutes after application of matricol as well as 24 hours after the treatment, in each case compared to the time prior to the application on the respective day of application. Furthermore, a corresponding assessment of the parameters was carried out by the test physician approx. 15 minutes subsequent to the application of Matricol.

Assessment Parameters:
  Reduction of erythema
  Calming of the skin
  Pleasant feel of the skin
  Normalization of blood supply
  Intensity of telangiectasia (assessment by the physician)
  Reduction of sensations such as burning, itching, tingling, numbness (assessment by the patients after 24 hours)

During a total of 28 applications, a topical antibiotics therapy moreover took place at the same time (cream treatment), while 13 applications were carried out without any antibiotics therapy at the same time. On the whole, it became evident that the observed effects of improvement occurred both in applications with simultaneous administration of antibiotics as well as in applications without antibiotics treatment. Conversely, no change of the condition of the skin due to the application became evident either in the matricol applications with simultaneous antibiotics therapy (results not shown in detail). Therefore, the clearly accomplished improvements of the condition of the skin after the matricol application could not necessarily be ascribed to the antibiotics treatment, but have to be considered as being independent from it.

The following fable shows the examined assessment parameters and gives the respective total number of assessments for each parameter from the total of 41 individual applications. In this case, a distinction is made between patients with a low intensity and a high intensify of the disease. Moreover, the results according to the assessments of the patients 15 minutes after application as well as 24 hours and the assessment of the test physician 15 minutes after the application are presented side by side. In this case, (+) marks an improvement, and (−) marks an unchanged state.

| | Assessment | | | | | | | | | | | |
|---|---|---|---|---|---|---|---|---|---|---|---|---|
| | Reduction of erythema | | Calming of the skin | | Pleasant feel of the skin | | Normalization of blood supply | | Intensity of telangiectasia | | Reduction of sensations such as burning, itching, tingling, numbness | |
| | + | − | + | − | + | − | + | − | + | − | + | − |
| Patient after 15 minutes | | | | | | | | | | | | |
| Slight intensity | 16 | 5 | 17 | 1 | 20 | 1 | 17 | 4 | | | | |
| Severe intensity | 19 | 1 | 12 | 2 | 20 | 0 | 17 | 3 | | | | |
| Physician after 15 minutes | | | | | | | | | | | | |
| Slight intensity | 16 | 5 | 17 | 1 | 21 | 0 | 17 | 4 | 15 | 6 | | |
| Severe intensity | 19 | 1 | 18 | 2 | 20 | 0 | 18 | 2 | 17 | 3 | | |
| Patient after 24 hours | | | | | | | | | | | | |
| Slight intensity | 9 | 8 | 11 | 4 | 14 | 3 | 12 | 5 | | | 11 | 5 |
| Severe intensity | 17 | 3 | 17 | 3 | 19 | 1 | 17 | 3 | | | 17 | 4 |

Example 3

Use of Freeze-Dried Layered Collagen Matrices in the Treatment of Induced Inflammatory Skin Diseases (Lesions) as a Consequence of a Local Treatment of Actinic Keratosis with Immunostimulants As a consequence of 4 weeks' treatment (in each case on Mondays, Wednesdays and Fridays) of an actinic keratosis in the face, above the eye brow below the hairline, with aldara (active substance imiquimod), a substance with an immunostimulating action, desired inflammatory reactions occurred on and around the affected area of the skin.

An area of 2-3 cm diameter was affected.

The affected area of the skin was swollen, severely reddened and very sensitive to pain.

After the treatment had been completed, the inflammatory reaction that had occurred was first treated by applying (twice daily) pyoloysin ointment (active substance combination: pyolysin+zinc oxide+salycic acid). However, no improvement of the inflammatory reaction could be obtained thereby.

Then, a treatment with layered freeze-dried collagen matrices having a collagen content>90% by wt. was carried out.

For the treatment, the layered collagen materials were cut to the size of the defect, moistened with water and laid on the affected area of the skin for 20 min.

At the beginning of the treatment, the collagen materials were applied twice one immediately after the other, so that the affected area of the skin was covered with the collagen material for a total of about 40 min.

A significant improvement of the sensitivity to pain and pressure as well as an alleviation of the stinging of the irritated skin was evident already after the second application on the first day. Even after the removal of the collagen dressing, this effect persisted for about 2 h.

The treatment was continued for another week, once daily, after cleaning the affected region of the skin with warm water. After the removal of the collagen dressing, a conventional moisturizing care product was applied in each case to the entire face.

Result of the Treatment:

In addition to the pleasantly cooling effect, a very fast anti-inflammatory and decongestant, and connected therewith a fast pain-relieving action was evident.

After one week's application, the affected area of the skin was no longer raised and reddened. A residual skin discoloration, which is often experienced to occur due to the elimination of the keratosis, gradually assimilated to the other skin color.

Comparative treatment of similar defects in the face, at the temple, as a consequence of the treatment of actinic keratosis with aldara, using exclusively pyolysin ointment, was able to produce a comparable treatment result after a treatment time of 1 month at the earliest.

Example 4

Use of Freeze-Dried Layered Collagen Matrices in the Treatment of Allergic Skin Reactions with Severe Erythema and Overheating of the Tissue, Severe Itching and Wheal Formation as a Consequence of a Systemic Antibiotics Therapy As a consequence of 12 days of a systemic (oral) antibiotics therapy, local allergic skin reactions in the form of severe erythema and overheating of the tissue, severe itching and wheal formation on the upper chest and the area of the neck occurred in a female patient (35 years).

In a semilateral test, a layered freeze-dried collagen matrix of the brand Matricol® with a collagen of >90% by wt. that was moistened with water, and on the other side, a conventional cotton or gauze dressing moistened with water was laid on the affected areas of the skin. The duration of the application was about 20 min.

The two materials were compared with regard to applicability and handling, wearing comfort as well as, in particular, the influence on the symptoms and complaints present.

Result of the Treatment:

The freeze-dried collagen matrix was characterized by significantly simpler and easier handling. Due to the high conformability and elasticity of the moistened material, it could be applied to the affected regions of the skin particularly well and retained its optimum position even in motion and in the case of an erect body posture.

In contrast, the gauze pad showed significantly poorer adhesion and application properties.

Moreover, the collagen matrix had a high level of moisture over the entire period of application, whereas the gauze pad dried already after a short time, which in that case also led to the drying pad not remaining on the treatment area anymore in the case of an erect body posture.

The extremely high cooling effect of the moistened collagen matrix and the significant reduction of itching were particularly noticeable. This advantageous effect persisted for at least 60 minutes even after the application. It was impossible to obtain an effect that even came close to this with the moist gauze pad.

Moreover, the skin treated with the collagen matrix felt significantly softer and more elastic than the other regions of the skin.

The invention claimed is:

1. A method of treating inflammatory and degenerative skin diseases and damage to the skin connected therewith in a patient in need thereof, the diseases selected from the group consisting of psoriasis, dermatitis, neurodermitis, atopical dermatitis, rosacea, hives, itching, skin eczema or eczematous changes, erythema, actinic keratosis, and inflammatory lesions as a consequence of a local treatment of actinic keratosis with immunostimulants, the method comprising
   (a) applying a flat dressing, sheet, pad, or mask consisting of freeze-dried dehydrothermally or chemically cross-linked collagen to the skin.

2. The method of claim 1, wherein the collagen is selected from the group consisting of porcine, equine and bovine collagen.

3. The method of claim 1, wherein the collagen in the collagen containing preparation consists of the following fractions:
   (a) fibrous insoluble collagen,
   (b) acid-soluble collagen, and
   (c) collagen peptides.

4. The method of claim 1, wherein the skin diseases or damage to the skin are characterized by at least one selected from the group consisting of tightness, erythema, heat, itching, scaling, eczematous changes, blisters, wheals or pustules.

5. The method of claim 1, wherein the flat dressing, sheet, pad or mask consisting of freeze-dried dehydrothermally or chemically cross-linked collagen is provided in the form of a kit-of-parts combination, comprising the freeze-dried collagen dressing, sheet, pad or mask on and an activator solution selected from the group consisting of water, physiological solutions, and aqueous solutions containing at least one of an active substance and an auxiliary substance, in an associated spatial arrangement.

6. The method of claim 1, further comprising:
   (b1) moistening the freeze-dried collagen material with an activator solution selected from
      water, physiological solutions as well as aqueous solutions containing at least one active and/or auxiliary substance, and applying the moistened collagen material to the skin areas to be treated
      or
   (b2) applying the freeze-dried collagen material to the skin areas to be treated, and moistening the dry layered collagen material on the skin areas to be treated with an activator solution selected from water, physiological solutions and aqueous solutions containing at least one of an active substance and an auxiliary substance.

7. The method according to claim 6, wherein the moistened layered collagen materials remain on the skin area to be treated for up to 60 minutes.

8. The method according to claim 6, wherein the application is carried out topically.

9. A method of treating inflammatory and degenerative skin diseases and damage to the skin connected therewith in a patient in need thereof,
the diseases selected from the group consisting of psoriasis, dermatitis, neurodermitis, atopical dermatitis, rosacea, hives, itching, skin eczema, eczematous changes, erythema, actinic keratosis, inflammatory lesions as a consequence of a local treatment of actinic keratosis with immunostimulants,
the method comprising applying to the skin a flat dressing, sheet, pad or mask consisting of
(a) freeze-dried dehydrothermally or chemically cross-linked collagen and
(b) at least one selected from the group consisting of
   (i) active agents selected from the group consisting of silver-containing active substances, tacrolimus, pimecrolimus, antihistamines, polidocanol, frankincense, frankincense extract, capsaicin, tannin, dexpanthenol, inorganic selenium compounds, organic selenium compounds, zinc, zinc salts, phospholipids, cholesterol sulfate, sphingolipids, urea, amino acids, carboxylic acids, pyrrolidone carboxylic acid, sodium, potassium, calcium, magnesium, lactate, lactic acid, citrate, chloride, phosphate and
   (ii) auxiliary substances selected from the group consisting of triglycerides, triclycerides of caprylic acid, triglycerides of capric acid, and triglycerides of combinations of capric acid and caprylic acid.

* * * * *